United States Patent [19]

Sitte et al.

[11] Patent Number: 4,745,764

[45] Date of Patent: May 24, 1988

[54] METHOD AND DEVICE FOR METAL-MIRROR CRYOFIXATION OF BIOMEDICAL OR SIMILAR TECHNICAL SPECIMENS

[75] Inventors: Hellmuth Sitte, Seefeld, Austria; Helmut Hassig, Homburg-Saar; Klaus Neumann, Bexbach-Sarr, all of Fed. Rep. of Germany

[73] Assignee: Reichert-Jung Optische Werke A.G., Fed. Rep. of Germany

[21] Appl. No.: 78,304

[22] Filed: Jul. 27, 1987

[30] Foreign Application Priority Data

Jul. 30, 1986 [DE] Fed. Rep. of Germany ....... 3625695

[51] Int. Cl.$^4$ ................................................ F24F 3/16
[52] U.S. Cl. ...................................... 62/78; 62/514 R
[58] Field of Search ............................... 62/78, 514 R

[56] References Cited

U.S. PATENT DOCUMENTS

| | | | |
|---|---|---|---|
| 4,302,950 | 12/1981 | Sitte | 62/514 R |
| 4,306,425 | 12/1981 | Sitte et al. | 62/514 R |
| 4,531,373 | 7/1985 | Rubinsky | 62/78 X |
| 4,563,883 | 1/1986 | Sitte | 62/514 R |
| 4,637,226 | 1/1987 | Sitte | 62/78 X |

*Primary Examiner*—Steven E. Warner
*Attorney, Agent, or Firm*—Alan H. Spencer

[57] ABSTRACT

A method for metal-mirror cryofixation of bio-medical or similar technical specimens in which a specimen is brought into contact with a highly polished, cooled metal mirror in order to cool at least a marginal zone of the specimen suddenly to a low temperature. In order to avoid deformation of the specimen caused by freezing, provision is made, immediately after the first contact between the specimen and the metal mirror, to press the latter against one another by an additional independent force until the specimen is completely frozen. A cryofixation device for this purpose comprises a force generating device, for example, a separate power storage device (135) which, under control, functions after contact between the specimen (106) and metal mirror (102), in other words exerts the additional force between the specimen and the metal mirror (FIG. 7).

18 Claims, 9 Drawing Sheets

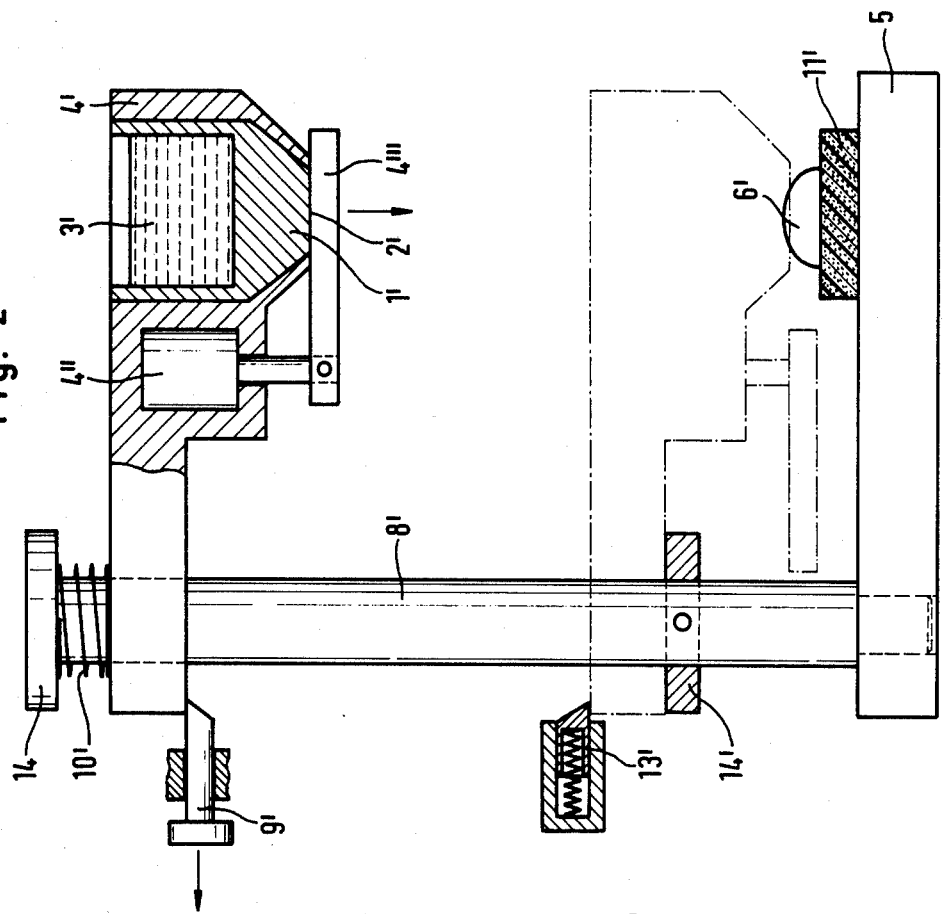
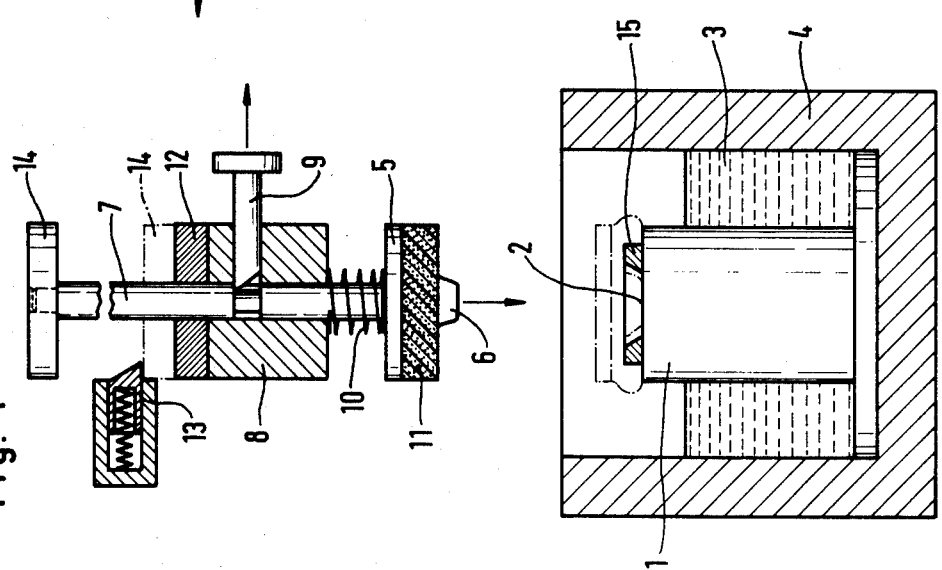

METHOD AND DEVICE FOR METAL-MIRROR CRYOFIXATION OF BIOMEDICAL OR SIMILAR TECHNICAL SPECIMENS

The invention relates to a method of metal-mirror cryofixation of biomedical or similar technical specimens with the features according to the preamble of claim 1. The invention also relates to a device corresponding to the preamble of claim 4 for working this method.

In addition to cryofixation by plunging specimens into a low-temperature bath (immersion cryofixation), metal-mirror cyrofixation is used for rapidly freezing specimens with a high moisture content, for example, biomedical specimens or technical specimens such as gelatins or suspensions which resemble them in their physical and chemical characteristics; in metal-mirror cryofixation the specimens are applied to a low-temperature solid surface polished to a high sheen. In this process, the specimen is cooled at least superficially so abruptly that separation of the aqueous or liquid mixed phases is either completely suppressed (vitrification) or is at least limited to a tolerable degree.

In metal-mirror cryofixation (also known as impact cryofixation) the specimen and the metal mirror are moved relatively to one another, in other words one of the two components (the specimen or the metal mirror) is fixed and the other is movable. The relative movement between the warm specimen and the cold surface of the metal mirror is intended to be terminated by their mutual contact. However, this is not usually the case (see BOYNE, A.F. Journal of Neuroscience Methods, 1, pp. 353-364, 1979) because as a result of the elastic layers used as a rule between the mostly rigid specimen holder and the specimen, which cannot be eliminated if one is to compensate for the irregular and only rarely reproducible three-dimensional shape of the specimen, as well as the elastic behavior of most biological specimens, as a rule, following the first contact between the specimen and the metal mirror, rebound phenomena (bouncing) occur in which the specimen or metal mirror, following a first elastic deformation of the specimen and/or the elastic intermediate layer, reverses its direction of motion. In most cases the initial contact is then interrupted at least once and, often, several times. Since the solid contact between the already suddenly-frozen marginal zone of the specimen and the metal mirror is broken, the heat flux changes, and the result is a more or less pronounced recrystallization of the already solidified areas, which as a result suffer a loss of quality for subsequent electro-optical investigation or are rendered completely useless. Measures have therefore been proposed for eliminating such rebound phenomena; these include, for example, arrangements for holding the system composed of the specimen holder/specimen/metal mirror by mechanical or magnetic retaining elements in the positional relationship reached in the intial contact (HEUSER et.al, J. Cel. Biol. 81, 1979:295).

It has also been found that in the case of larger inhomogeneous specimens in particular, forces are evidently created in the course of freezing which frequently lead to bending or twisting of the previously flat specimen surface, which results at the initial contact of the specimen as a replica of the surface of the metal mirror [sic]. From this, one can see that the final surface is curved either concavely or convexly. As a result of this deformation, the originally intimate contact between the specimen and the metal mirror is lost over large areas of the specimen surface. To the extent that the specimen is not yet completely frozen through, the loss of contact causes the initially perfectly frozen marginal layers of the specimen to recrystallize as a result of being warmed to more than $-80°$ C., thereby making them less valuable or completely useless for observation under the electron microscope. There have been many efforts at suppressing such phenomena. The simplest means proposed for this purpose is increasing the force with which the specimen and metal mirror are pressed against one another, whereby the spring force for pressing the specimen against the metal mirror or the mass of the specimen holder or the length of the travel path between the specimen holder and the metal mirror are increased. However, these measures do not result in the desired success because this also increases the speed with which the specimen and metal mirror strike one another. This produces strong artefactive deformations of the specimen (in other words, those produced by the preparation itself) which, in turn, sharply reduce the value of the results since the positional relationships of the various structural elements of the specimen, which they had in vivo, are destroyed. In view of the extremely irregular shapes which biological samples can have, these artefacts can never be completely eliminated even by using annular spacers which rest on the metal mirror and are intended to prevent the specimen from being crushed.

The measures listed above for preventing separation of the specimen and metal mirror caused by rebound are unsuccessful in this regard as well, because a positive contact between the specimen and the metal mirror can only be maintained only with a relatively strong initial application pressure. This therefore means that the previously warm specimen and the likewise warm specimen holder contract sharply when cooled. The application pressure initially required for this is turn produces a very rapid deformation of the type described above to produce artefacts. The contact cannot be maintained to the extent desired in all cases during the freezing process with a pre-selected rigid positional relationship between the specimen and the metal mirror. As a consequence, therefore, secondary recyrstallization of the specimen frequently occurs, always nonreproducibly, at the moment when the application pressure between the specimen and the metal mirror drops below the value required for good heat transfer. In the system described by BOYNE (op. cit.) deformation phenomena of the type described can in fact be largely eliminated, but the original excessive pressing of the specimen as a consequence of the impact velocity and the mass of the specimen holder cannot be avoided.

The goal of the present invention, therefore, is to provide a methodfor metal-mirror cryofixation and a device for working the method, by which readily deformable specimens of the type described can be frozen reliably, i.e., without artefactive deformations from the state they had in vivo. Specifically, the excessive pressure described caused by a high-impact velocity between the specimen and the metal mirror is to be avoided, but, however, without having to take into account the above-mentioned bending of the contact area between the specimen area and the metal mirror due to the lack of sufficient application pressure.

This goal is achieved according to the present invention by the procedure described in the characterizing clause of claim 1 and by the device described by the features in the characterizing clause of claim 4.

The invention is based on the fact that when a specimen, especially a larger specimen with a surface larger than 25 mm$^2$, strikes a cold metal mirror, the velocity at first and then the force, which appears as a result of the retardation of the moving mass, determine the deformations and damage to the specimen (for example, bursting of erythrocytes, horizontal flows or movements, and shearing forces in the specimen) which occur immediately on impact and before the freezing of the marginal zone. This damage evidently occurs during a space of time which is significantly less than the range of one millisecond, since the amorphous vitrification of the outermost marginal zone is definitely already completed in less than a millisecond. Since the specimen holder with its inertial mass continues its movement even after the initial contact between the specimen and the metal mirror, it produces immediately thereafter severe compression in the zones located behind the marginal zone of the specimen, which can be seen with increasing depth in the specimen. While these injuries are caused by the retardation of the mass of the specimen holder and the parts connected to it, the damage mentioned above is apparently caused by the retardation of the specimen. Therefore, according to the invention, they can only be avoided by reducing the impact velocity, while the other types of damage, in addition to reducing the impact velocity, can also be kept small by reducing the inertial mass coupled to the specimen.

Another fact which forms the basis of the invention is that it is necessary to press the surfaces of the specimen and the metal mirror in contact with one another with a relatively high application pressure of, for example, more than 0.5 kg/cm$^2$, but this application pressure must remain independent of the application pressure produced by the impact between the specimen and the metal mirror in order to avoid the above-mentioned bending of the contact surface of the specimen and to keep the specimen and metal mirror in a positive solid contact until the specimen is completely frozen.

Finally, a prerequisite for the success of the method according to the invention and the device used therefor, is prevention of rebounding phenomena which, following impact between the specimen and the metal mirror, cause reversal of the direction of movement and cause a resultant separation of the specimen and metal mirror.

In view of the independence of the additional force, which produces the application pressure, from the velocity with which the specimen and metal mirror strike one another, it is possible on the one hand to reduce this velocity to the point where the above-mentioned damage does not occur in the area of the suddenly frozen marginal zone of the specimen, or, on the other hand, to increase the above-mentioned minimum application pressure of, for example, more than 0.5 kg/cm$^2$ and to maintain it during the entire freezing process, thus ensuring a good solid contact between the specimen and the metal mirror and the resultant optimal heat flux through the contact zone, preventing the above-described bending of the contact surface of the specimen. These advantages are supported by the prevention of rebound phenomena and by damping of the impact process by elastic means.

According to an advantageous embodiment of the method according to the invention and the device used therefor, provision is made such that the additional force which produces the application pressure following the initial contact is adjustable or pre-selectable, in order thereby to achieve adaptation to different specimens. Accordingly, the velocity for the approach of the specimen and the metal mirror to one another can be made adjustable or pre-selectable so that two independent systems are used for the original application pressure at first contact and for the application pressure to be maintained thereafter. However, separate systems are not absolutely necessary for this purpose within the scope of the invention; it is also possible to effect the approach, as well as the pressing of the specimen and metal mirror against one another, by a system within whose framework, for example, the time of the initial contact between the specimen and the metal mirror is automatically detected by means of a sensor and the force already producing the motion, from this point on, is adjusted and controlled to the higher value required for the necessary application pressure. This can be accomplished, for example, in the following manner: Upon actuation of the movable specimen holder or the movable metal mirror by a pneumatic, hydraulic, or magnetic system, the initial contact between the specimen and metal mirror is detected by a sensor, microswitch or other control element, and the initially lower pressure sufficient for movement in the pneumatic or hydraulic system, or the lower magnetic flux in a magnetic coil, is increased in controlled fashion.

Further embodiments of the method according to the invention as well as technical implementations for the device according to the invention will be apparent from the subclaims.

Devices according to the state of the art as a point of departure for the invention, as well as embodiments of the device according to the invention, will be described in greater detail below with reference to the enclosed drawings.

FIGS. 1 and 2 show purely schematic, partially cut-away side views of devices for metal-mirror cryofixation according to the state of the art;

Figure 18:
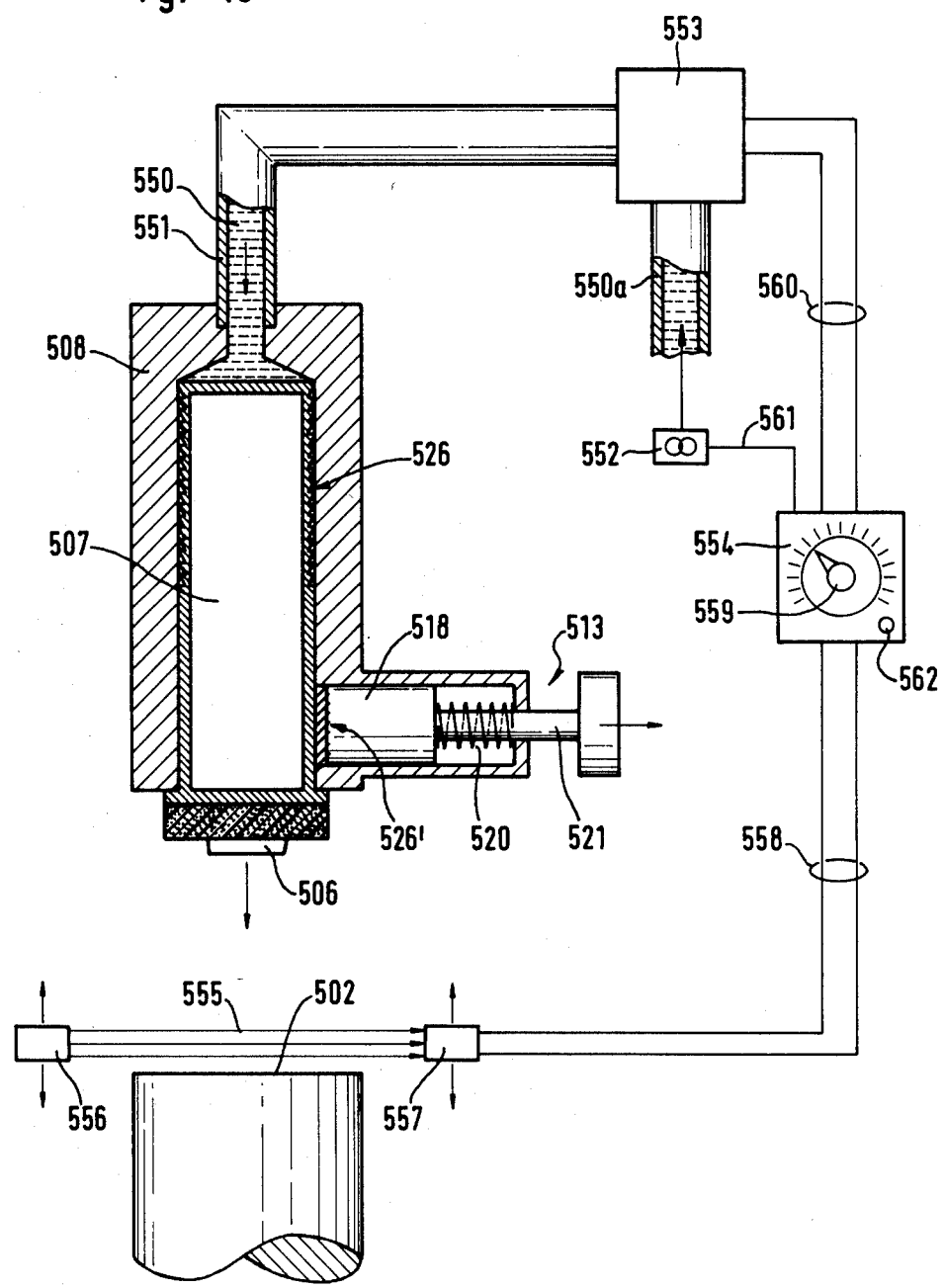
Figure 19:
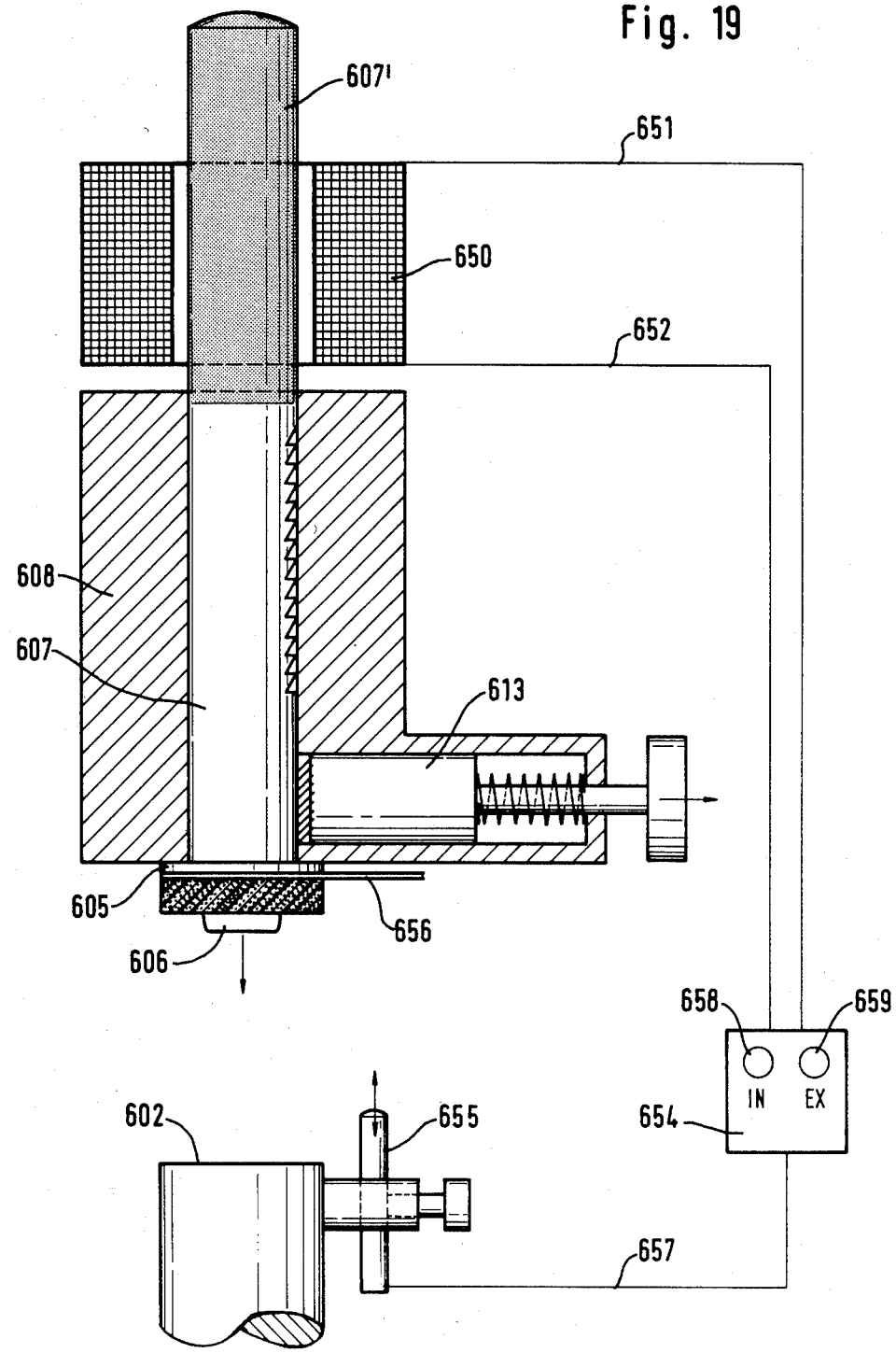

FIG. 18 is a schematic side view, partially cut away, of a fifth embodiment of the device according to the invention in a pneumatic or hydraulic drive for moving the specimen holder and for producing the application pressure, and FIG. 19 is a side view, partially cut away, of a sixth embodiment of the device according to the invention with an electromagnetic drive device for moving the specimen and generating the application pressure.

The device shown in FIG. 1 for metal-mirror cryofixation according to the state of the art, comprises a low-temperature solid body 1, which has a highly polished upper end surface 2, the metal mirror, and in which a container 4 containing a liquid cryogen 3, for example, liquid nitrogen, is disposed. Above metal mirror 2 is an injection device consisting of a specimen holder 5 for a specimen 6, an injection rod 7, slidably mounted in an injector holder 8 and held in its position by a trigger pin 9, which can engage an annular groove in injection rod 7, as well as a power storage device in the form of a compression spring 10 pretensioned in the intial position of injection rod 7. Specimen 6 is held by means of an elastic intermediate layer 11 against specimen holder 5 rigidly connected to injection rod 7, said layer 11 consisting for example of felt or foam. A blocking device to prevent rebound of specimen 6 off metal mirror 2 is associated with the injection device, of which device two optionally usable embodiments are shown in FIG. 1: a locking pin 13 tensioned by a compression spring which, following impact of specimen 6 on metal mirror 2, in other words in the lowermost position of injection rod 7, can snap behind an end plate 14 at the end of injection rod 7, as well as a powerful magnet 15 disposed above injector holder 8, said magnet holding end plate 14, made of ferromagnetic material, in its lowermost position.

A spacer in the form of a ring with an inside wall tapering conically downward is disposed on metal mirror 2, said spacer being intended to prevent excessive crushing of specimen 6 when it strikes metal mirror 2.

FIG. 2 shows an "inverse mirror system" in which specimen 6' is fastened in position on a specimen holder 5' by an elastic intermediate layer 11', for example by needles. Metal mirror 2' is formed in a pot-shaped body 1' which contains cryogen 3' and is held in a holder 4'. A swivel device 4" is incorporated into holder 4' for a protective cover 41''', which can be swiveled away under control before metal mirror 2' strikes specimen 6'. Holder 4' is slidably and displaceably guided on an injector holder 8' and held in its initial position by a trigger pin 9'. A power storage device in the form of a compression spring 10' to accelerate holder 4' is provided between an upper end plate of injector holder 8' and the top of holder 4'. In this inverted system as well, holder 4' can be prevented by a mechanical locking device 13' or a magnetic locking device 14' from rebounding off object 6' after striking it. Since the results which can be achieved with the devices which according to FIGS. 1 and 2 correspond to one another and the shortcomings initially described apply to both, in the following the function of the known devices and also those of the devices according to the invention to be described later on will be explained with reference to the embodiment in which the metal mirror is fixed and the specimen is moved, according to FIG. 1.

The device according to FIG. 1 functions as follows: After trigger pin 9 is pulled, injection rod 7 with specimen 6 fastened to it moves under the influence of gravity and is impelled by the force of compression spring 10 with acceleration downward in the direction of metal mirror 2. When specimen 6 strikes low-temperature metal mirror 2, a marginal zone of specimen 6 is suddenly deep-frozen as a result of the pronounced heat transfer thus achieved. Spacer ring 15 prevents specimen 6 from being crushed by the force created by the retardation of injection rod 7 and the additional mass contained therein. In addition, locking devices 13 or 14, 15 prevent specimen 6 from rebounding from metal mirror 2 as a result of the elastic properties of the specimen as well as elastic intermediate layer 11.

Figure 3:
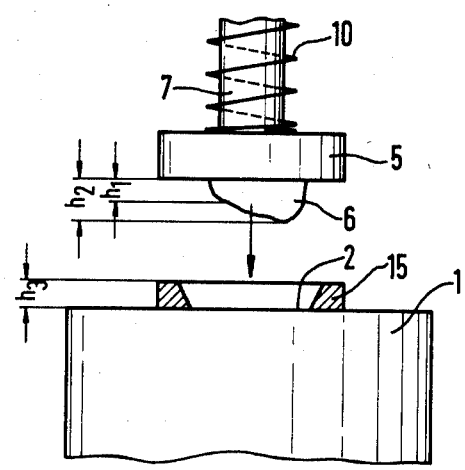
FIGS. 3–6 show details considered to represent the state of the art relating to the mounting of the specimen on a device according to FIG. 1.

FIGS. 3 to 6 show various embodiments of the specimen holder according to the state of the art, in which it is intended to avoid at least some of the damage done to specimen 6 described at the outset:

In the simplest specimen holder according to FIG. 3, specimen 6 is mounted directly on rigid specimen holder 5, for example, by means of adhesive. Since specimen 6 is immediately and completely crushed upon striking metal mirror 2, the above-mentioned spacer ring 15 is mounted on metal mirror 2 to protect it, the height of said ring having to be adjusted precisely to the shape of the specimen, so that, for example, $h_1 < h_3 < h_2$. Specimen 6 is then compressed to the average height $h_3$ of spacer ring 15.

Figure 4:
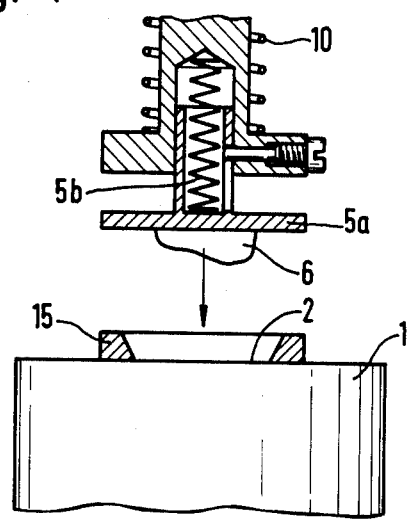
Figure 5:
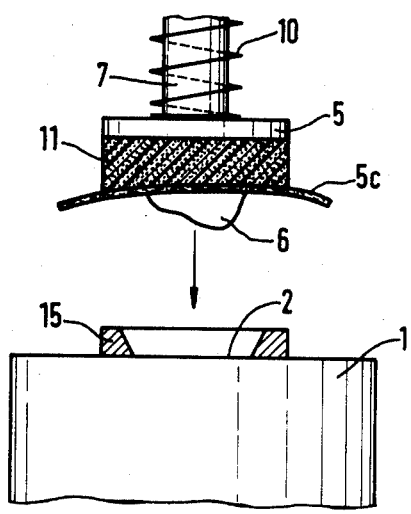

Harmful deformations are intended to be prevented in the specimen holder according to FIG. 4 by a soft additional spring 5b, by which specimen holder 5a rests against the injection rod. This embodiment, however, has been abandoned in practice in favor of the specimen holder shown in FIG. 5 wherein an elastic intermediate layer 11 made of foam is provided (see also FIG. 1), whereby specimen 6 is separated from intermediate layer 11 by an anti-adhesive plastic film (polyethylene, for example) or moistened filter paper 5c.

Figure 6:
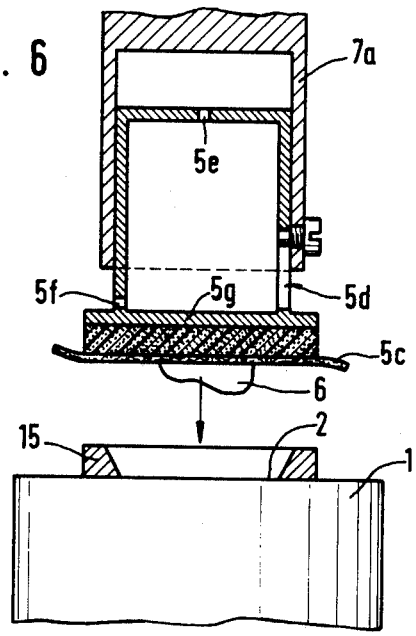

However, the best results are achieved with a specimen holder, according to FIG. 6, which provides for pneumatic damping (see DE OS No. 3532446). Here an injection rod 7a of larger diameter receives a hollow cylinder 5d of smaller mass as a piston, which is initially in its lowermost position and, following initial contact between specimen 6 and mirror surface 2, cushions the impact with the air cushion in its cavity, thereby keeping the deformation of specimen 6 within limits. The air initially trapped in hollow cylinder 5d slowly escapes through openings 5e and 5f until finally specimen holder 5g has reached its uppermost position, defined, for example, by an end stop.

As stated at the outset, the known devices described have in common the fact that the suppression of rebound gives satisfactory results only if very high velocities and/or masses associated with the specimen holder are used by which the specimen and the elastic intermediate layer, if any, are compressed so strongly that, following stopping of the moving parts, sufficient pretensioning is retained to suppress the described bending or twisting of the contact surface of the specimen as well as the lifting of this surface off the metal mirror, which is necessarily associated therewith. However, even with high initial pretensioning, permanent contact between the specimen and the metal mirror can only be achieved when the spacer ring described above is very precisely adjusted to the geometry of the specimen. In view of the speed with which preparations of this kind must be made, such adjustment is usually not possible, however. In addition and in particular, there is the fact that even in those cases in which such adjustment is in fact accomplished, the specimen is so defined by the high velocity and masses and resultant forces that in many instances, despite optimum cooling, it is no longer usable for morphological investigation. This is especially true for the larger specimens of interest today in which the contact area between the specimen and the metal mirror is often much greater than 25 mm$^2$.

Figure 7:
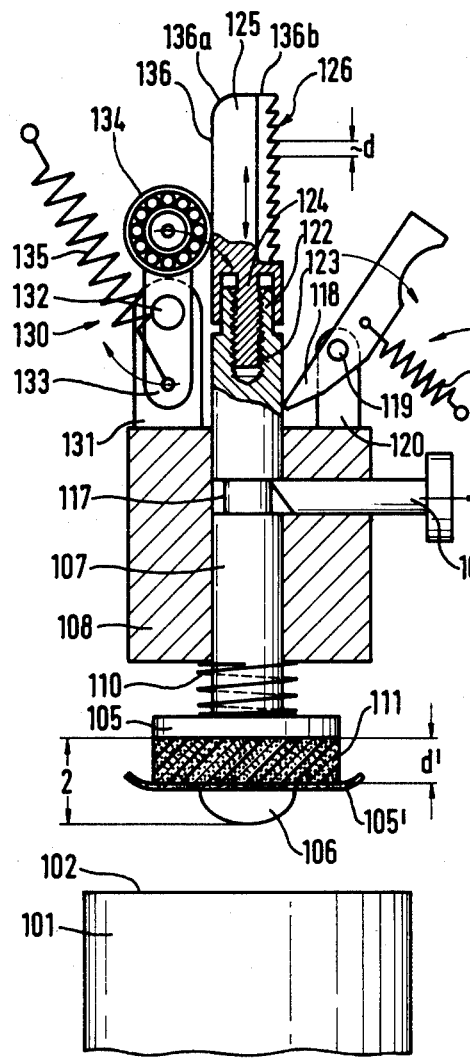
FIG. 7 is a schematic side view, partially cut away, showing the parts essential to the invention in a first embodiment of a device according to the invention in the initial state.
Figure 8:
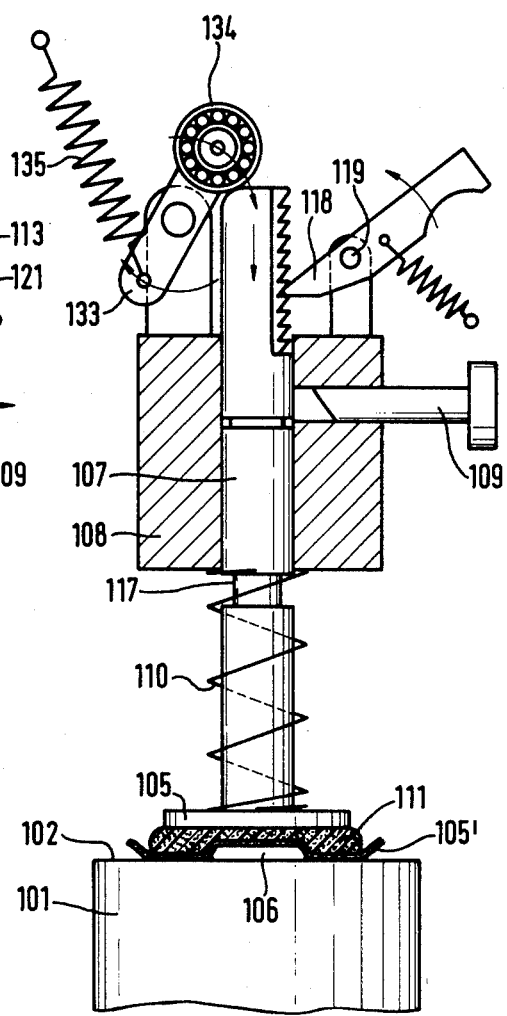
FIG. 8 shows the device according to FIG. 7 in the state representing impact of the speciment against the metal mirror.

The first embodiment of a device according to the invention according to FIGS. 7 and 8 has a metal body 101 built and arranged in similar fashion to the devices according to the state of the art described above, whose highly polished upper end face 102 forms a metal mirror. As a result of the similarity in this regard to known devices, further details have been eliminated from the drawing. Specimen 106 is fastened to a specimen holder 105 by means of an anti-adhesive film 105' made of polyethylene, for example, and an elastic intermediate layer made of felt or foam 111, which is integral with the lower end of an injection rod 107. Injection rod 107 is slidably and displaceably guided in an injector holder 108, which is fastened, in a manner not described in greater detail, to a frame or a housing. Injection rod 107 has an annular groove 117 into which, with injection rod 107 in the initial position shown in FIG. 7, the beveled end of a trigger pin 109 projects, thereby holding injection rod 107 in this initial position. In addition, injection rod 107 is subjected to a downward force by a first power storage device in the form of a pretensioned compression spring 110, fitted between the upper end of specimen holder 5 and the lower surface of injector holder 108.

A locking device, represented completely by 113, is disposed at the upper end of injector holder 108 to prevent rebound. This locking device 113 comprises a locking latch 118, which is pivotable by means of a shaft pin 119 on a bearing block 120 about an axis which is perpendicular to the plane of the drawing in FIG. 7. One end of an extension spring 121 is attached to the arm above shaft pin 119, the other end of said spring being fastened to the housing or frame, not shown, and urging locking latch 118 in the direction indicated by the arrow. As a result, the tip of locking latch 118 is forced elastically against the outer surface of injection rod 107.

As follows from FIG. 7, the upper end of injection rod 107 is reduced to a projection 122 of smaller diameter and has a threaded bore 123. A corresponding threaded pin 124 of a control part 125 projects into this threaded bore 123, overlapping projection 122 of injection rod 107 with its lower hollow-cylindrical end, and itself constituting an extension of injection rod 107. Screwing further in or out changes the position of control part 25 relative to locking latch 118. A sawtooth profile 126 is provided on control part 25 on the part facing locking latch 118, over which profile, when injection rod 107 is moving downward, the tip of locking latch 118 can slide. The tips of the teeth on sawtooth profile 126 are separated from one another by a distance d which is much less than thickness d' of elastic intermediate layer 111.

On the side of injection rod 107 which is opposite locking device 113, a power storage device 130 for producing an application pressure is also provided on the top of injector holder 108. This comprises a bearing block 131 projecting upward and fastened to injector holder 108 with a bearing pin 132 on which a lever 133 is pivotably mounted approximately at the center of its length in a plane parallel to the plane of the drawing of FIG. 7. A roller-bearing-mounted roller 134 is rotatably mounted on the upper end of lever 132; a tension spring 135 is attached to the lower end of the lever, said spring being fastened to the housing, not shown, and urging lever 133 in the direction of the curved arrow. As a result, roller 134 abuts a lateral, curved surface 136 of control part 125. Curved surface 136 is largely flat and in a first segment runs parallel to the common lengthwise axes of injection rod 107 and control part 125. In the vicinity of the upper end of control part 125, curved area 136, which has been flat unit this point, takes on a curvature 136a, circularly cylindrical for example, and blends into a curved segment 136b at the upper end of control part 125, which is perpendicular to the above-mentioned lengthwise axis.

The operation of the injector device according to FIGS. 7 and 8 is as follows: After specimen 106 is placed on specimen holder 105, rotating injection rod 107 relative to control part 125 adjusts the latter relative to power storage device 130 in such fashion that upon initial contact between specimen 106 and metal mirror 102, roller 134 is located exactly at the end of curved curve segment 136 and at the beginning of the upper flat curve segment 136b. When injection rod 107 is released by pulling trigger pin 109 out of annular groove 117, it move under the influence of gravity, as well as the force of spring 110, downward with increasing velocity until specimen 106 strikes metal mirror 102. During this downward movement, the tip of locking latch 118 initially slides along the outer surface of injection rod 107 and control part 125 and then over the teeth of sawtooth profile 126. Due to the relatively weak force of spring 110, the velocity of injection rod 107 and hence of specimen 106 remains considerably less at the end of the movement path, in other words, on striking metal mirror 102, than in the devices according to the state of the art described at the outset. When specimen 106 reaches the end of the movement path, at which movement has stopped (see FIG. 8), rebound caused by elastic return of the elastic elements involved is reduced at least to a degree, which is greater than or the same as tooth spacing d, by virtue of the fact that the tip of locking latch 118 has engaged a tooth space in sawtooth profile 128.

During the downward movement of injection rod 107, roller 134 also rolls along curved surface 136. Apart from unavoidable friction in the roller bearing of roller 134 and in the slide guide of injector holder 108 for injection rod 107, the velocity of injection rod 107 is not affected as long as roller 134 is on the axially parallel part of curved surface 136. Near the end of the movement path of specimen 106, however, roller 134 begins moving along the curved section 136a of the curved surface so that the spring force of spring 135 is converted to an increasing degree by lever 133 and roller 134 into a force acting in the direction of the lengthwise axis of injection rod 107. This causes a rapidly increasing pressure of specimen 106 against metal mirror 102, which at the outset can be set by the above-mentioned adjustment of control part 125 relative to the power storage device 130. The device therefore meets the requirements according to the invention without using complicated elements: On the one hand the velocity, when specimen 106 strikes metal mirror 102, is determined exclusively by the stiffness of spring 110 and can be varied within wide limits by changing the spring tension. On the other hand, the force with which specimen 106 is pressed against metal mirror 102 during freezing is produced by power storage device 130, independent of spring 110, independently of the pretensioning of spring 110 by an appropriate pretensioning or selection of spring 135. Thus, with a slow, gentle placement of specimen 106, the result is a large deformation-free vitrification of the marginal zone of the specimen, thus preventing bending or twisting of the specimen during freezing as a result of the increase in application pressure by means of power storage device 130, and thus preventing the recrystallization processes described at the outset as well.

Following completion of the freezing process, injection rod 107 can be raised back to its original position after releasing locking latch 118 by lifting it outward in the direction of the arrow shown in FIG. 8.

Figure 9:
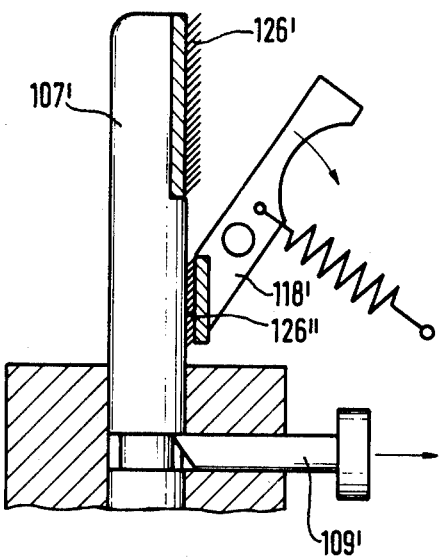
FIG. 9 is a modification of the locking device used in the embodiment according to FIGS. 7 and 8 for preventing rebound.

FIG. 9 shows a modification of locking device 113 in which sawtooth profile 126 is replaced by a brush 126' with flexible bristles or wire pins directed diagonally upward, and the tip of locking latch 118 is replaced by another brush 126'', whose bristles are inclined in a direction opposite to the bristles of first brush 126'. The function of this locking device corresponds to that shown in FIGS. 7 and 8, in other words, during the downward movement of injection rod 107', brush 126'' of locking latch 118' slides over brush 126', but prevents rebound of injection rod 107' by hooking. With this locking device, one of the two brushes 126' and 126'' can also be replaced by a sawtooth profile similar to that shown in FIG. 7.

Figure 10:
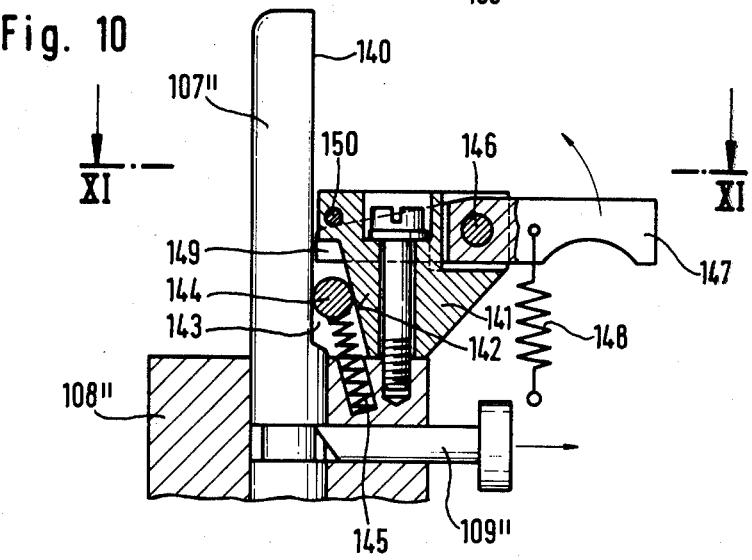
FIGS. 10 and 11 show a side view and a partial top view of another modification of the locking device used in the embodiment shown in FIGS. 7 and 8 for preventing rebound.
Figure 11:
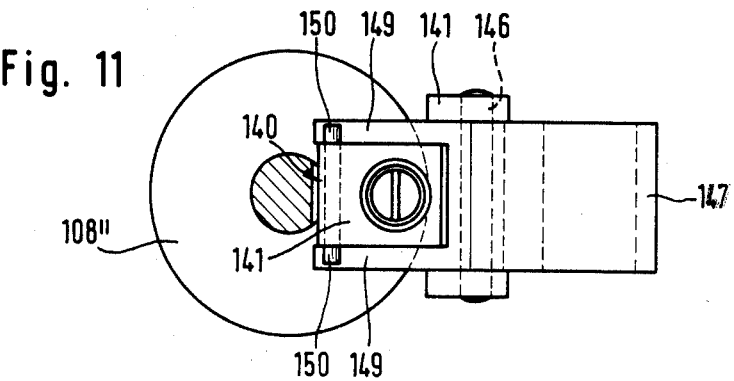

The locking device according to FIGS. 10 and 11 operates according to the principle of a roller clutch. Injection rod 107'' in its upper end segment has a plane travel surface 140. On the top of injector holder 108'' is a locking element 141, which has a matching surface 142 which is diagonal with respect to the lengthwise axis of injection rod 107'' and tapers upward toward the latter. Travel surface 140 and matching surface 142 form a wedge-shaped slot 143 through which a clamping roller 144 passes transversely perpendicularly to the plane of the drawing in FIG. 10. Clamping roller 144 is urged into wedge-shaped slot 143 by a compression spring 145 mounted in a hole in injector holder 108''. On the side opposite matching surface 142, locking element 141 has a recess trasversed by a bearing pin 146. A pivot lever 147 is mounted on this bearing pin, one arm of said lever being urged downward by a tension spring 148 and its other arm being divided into two fork arms 149 which surround in their vicinity locking element 141 (see FIG. 11). Fork arms 149 have their ends each abutting a stop pin 150 projecting laterally from locking element 141.

When injection rod 107'' is accelerated downward by release of trigger pin 109'', as described above in conjunction with the embodiment according to FIGS. 7 and 8, clamping roller 144 rolls or slides during the downward movement along the travel surface 140 without perceptibly hindering the downward movement. When injection rod 107'' has reached the end of its travel path, its return movement as the result of an elastic rebound is prevented by jamming of the spring-tensioned clamping roller 144 in wedge-shaped slot 143. This locking device is independent of a spacing d as is provided, for example, in the locking device according to FIGS. 7 to 9, and can therefore suppress even a very small rebound of injection rod 107''. To return injection rod 107'' to its initial position, the locking device can be released after cryofixation is complete by raising fork-shaped pivot lever 147 against the force of spring 148 in the direction of the arrow in FIG. 10, so that the free ends of fork arms 149 force clamping roller 144 downward and out of wedge-shaped slot 143.

Figure 12:
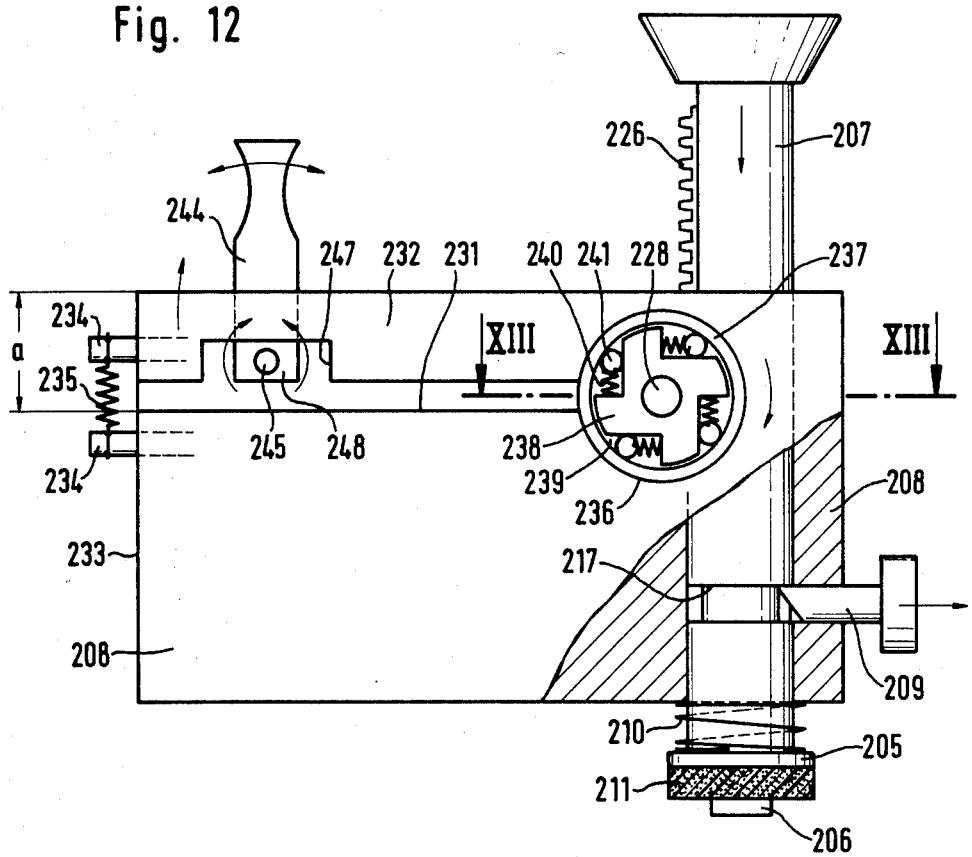
FIG. 12 is a side view, partially cut away, of the parts essential to the invention in a second embodiment of the device according to the invention.
Figure 13:
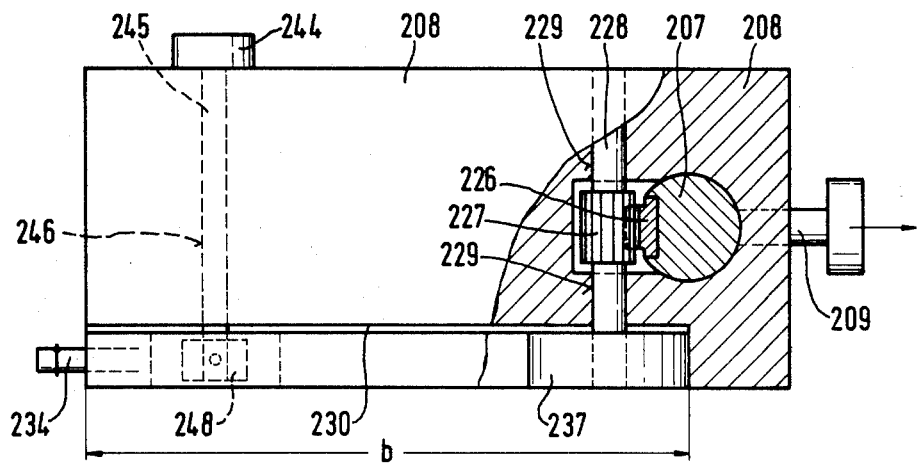
FIG. 13 is a top view and a partially cut-away view along Line XIII—XIII in FIG. 12.

FIGS. 12 and 13 show a second embodiment of the device according to the invention of which again only the part relating to the injector device is shown. The other components of the device, for example the cooled metal mirror, are designed and located in the same fashion as already described in connection with the devices according to the state of the art.

An injection rod 207 is slidably and displaceably mounted in a hole in an injector holder 208 which in turn is part of a housing or the like not shown. Injection rod 207 has an annular groove 217 into which the beveled end of a trigger pin 209 projects, holding the injection rod in the initial position shown in FIG. 12. A pretensioned soft compression spring 210 abuts the underside of injector holder 208, said spring tensioning the back of a specimen holder 205 made integral with injection rod 207. A specimen 206 is mounted by an elastic intermediate layer 211 on specimen holder 205.

A rack 226 is mounted on injection rod 207, said rack meshing with a pinion 227. Pinion 227 is made integral with a rotational shaft 228, rotatably mounted in a bearing bore 229 of injector holder 208. On the side of injector holder 208 a clamping arm 232 made integral with injector holder 208 is formed by a slot 230 made to a depth a and extending over length b, running parallel to the side edge (FIG. 13) of injector holder 208 and by a cut 231 running perpendicular to slot 230, said arm being elastically movable to a certain degree. At the end of clamping arm 232, in other words above cut 231 and below cut 231, retaining pins 234 are mounted in side surface 233 of injector holder 208, between which pins a tension spring 235 is stretched. At the right end (FIG. 12) of cut 231 the latter expands to form a circular recess 236 to receive a conventional free-running element 237 (cf. "Der Maschinenmarkt" No. 65, 1959: "A roller clutch as a new machine element"). Free-running element 237 comprises a circular annular housing in which a rotor 238 is rotatable, said rotor being non-rotatably mounted on the end of rotation shaft 228 which projects into recess 236. Rotor 238, by virtue of appropriate recesses, forms four wedge-shaped chambers 239 into which clamping rollers 241 are forced by compression springs 240. On the side of injector holder 208 which is opposite clamping arm 232, a lever 244 pivotably in the direction of the double arrow shown is mounted by a shaft 245 which traverses a hole 246 in injector holder 208 and has mounted non-rotatably at its end which projects into an expansion 247 of cut 231, a pressure element 248. Pressure element 248 in the position shown in FIG. 12 has its flat upper side abutting the correspondingly flat wall of expansion 247 in plane fashion. Tension spring 235 bends clamping arm 232 downward in such fashion that it grips the housing of free-running element 237 in recess 236 and prevents it from rotating in any direction.

The operation of this embodiment is as follows: When injection rod 207 is released by pulling trigger pin 209 out of annular groove 217, spring 210 accelerates it in the same fashion as described above. During the downward movement, the linear movement of rack 226 is converted into a rotary movement of pinion 227, which also causes rotor 238 of free-running element 237 to rotate in the direction of the part shown in FIG. 12. This rotation is not opposed by clamping rollers 241. The housing of free-running element 237, as described above, is prevented from rotating by clamping arm 232. When specimen 206 reaches the end of its travel and the motion stops, reverse motion caused by elastic rebound is prevented by free-running element 237. The backward motion of rack 226 is opposed by pinion 227 which is prevented from turning in the opposite direction by clamping rollers 241. Clamping rollers 241 abut the walls of clamping chambers 239. In this manner, reverse movement even of very small extent can be prevented. Following completion of the freezing process, the positive clamping of the housing of free-running element 237 can be released by swinging lever 244 in either direction, since by swinging lever 244 over pressure element 248, clamping arm 232 is raised slightly against the action of tension spring 235 and against its own elastic fastening on injection element 208 so that the housing of free-running element 237 is freed. Free-running element 237 can then be turned backward as a unit against the normal direction of rotation indicated by the arrow so that injection rod 207 and be brought back to its initial position.

The third embodiment shown in FIGS. 14 and 15, as far as the locking device is concerned, largely corresponds to the embodiment just described with reference to FIGS. 12 and 13 with the exception that release lever 244 in this case is disposed on the same side as free-running element 237. For this reason the same reference numbers as in FIGS. 12 and 13 are used for corresponding parts.

However, the manner in which injection rod 307 is tensioned by a power storage device to achieve the movement of specimen 306 is different. In the present embodiment, there is no compression spring mounted on injection rod 307 corresponding to compression spring 210. Instead of rack 226, a flexible, toothed belt 326 is attached by a screw in the vicinity of the upper end of injection rod 307, said belt engaging pinion 227 and wrapping 90° around it and being under the pretension of a tension spring 350. Tension spring 350 is attached to an eye 351 at the end of toothed belt 326 and also to an adjusting device 352, and extends through a hole 353 in injector holder 308. Adjusting device 352 in the embodiment shown consists of a screw, screwed into a threaded bushing 354. Threaded housing 354 in turn is held in hole 353 by a clamping screw 355. By turning the screw to a greater or lesser degree out of threaded bushing 354, the pretensioning of tension spring 350 and hence the amount of force exerted on injection rod 307 can be changed. Instead of the very simple adjusting device 352 shown here, other elements can be used, for example, a self-locking, powered, threaded screw with a coarse pitch or a stepping motor.

Figure 14:
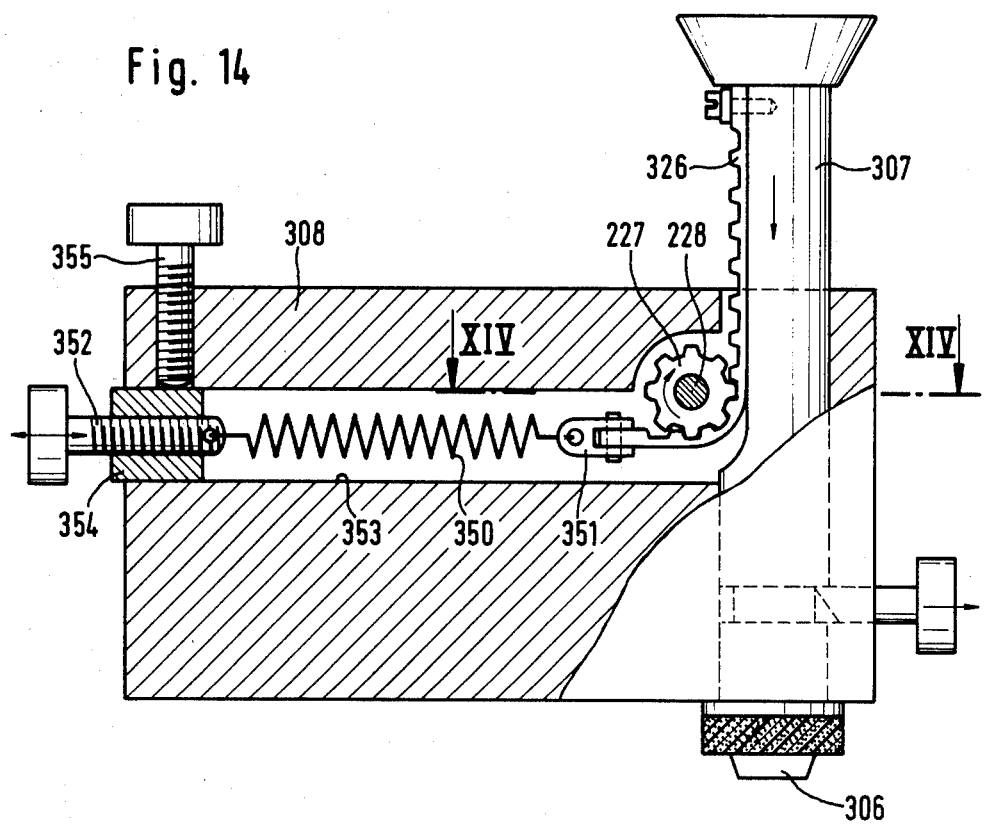
FIGS. 14 and 15 show arrangements similar to FIGS. 12 and 13 for a third embodiment of the device according to the invention.
Figure 15:
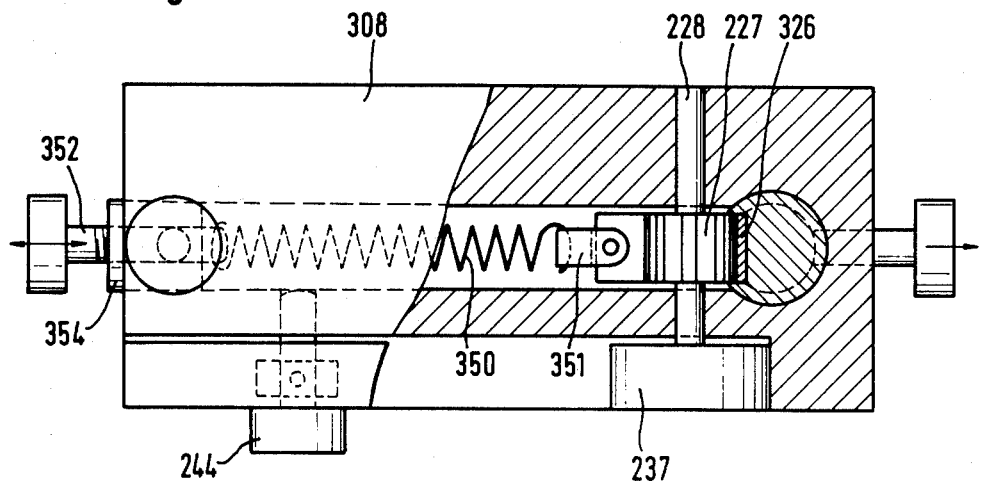
Figure 16:
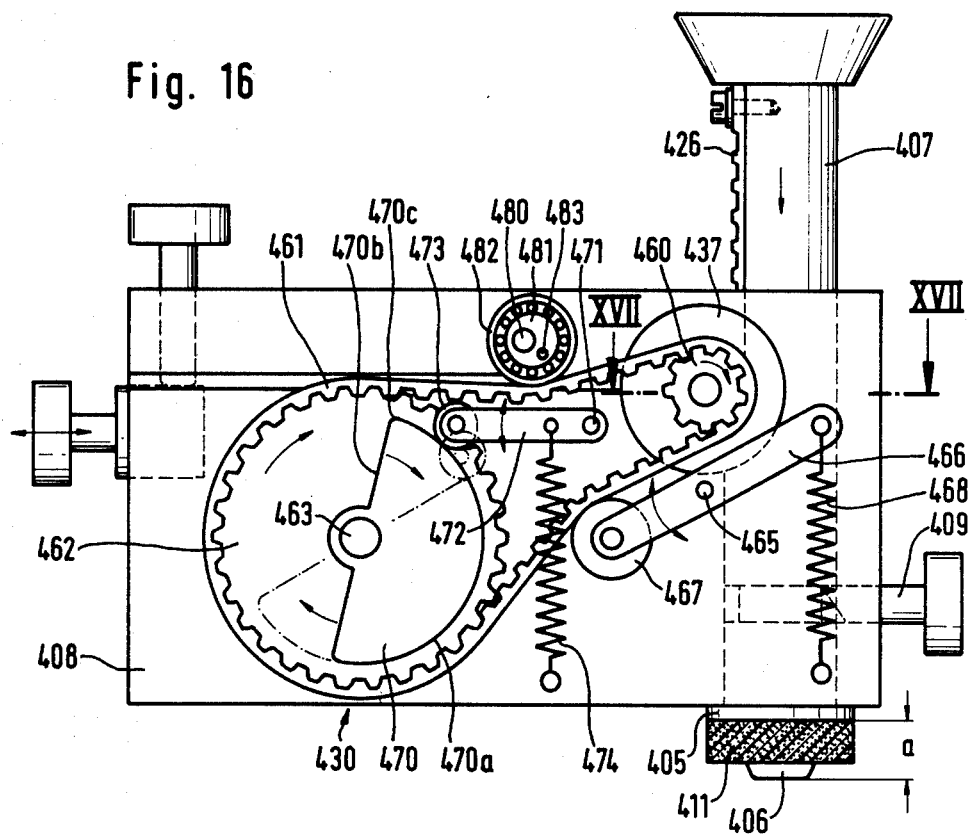
FIGS. 16 and 17 show arrangements similar to FIGS. 12 and 13 of a fourth embodiment of the device according to the invention.
Figure 17:
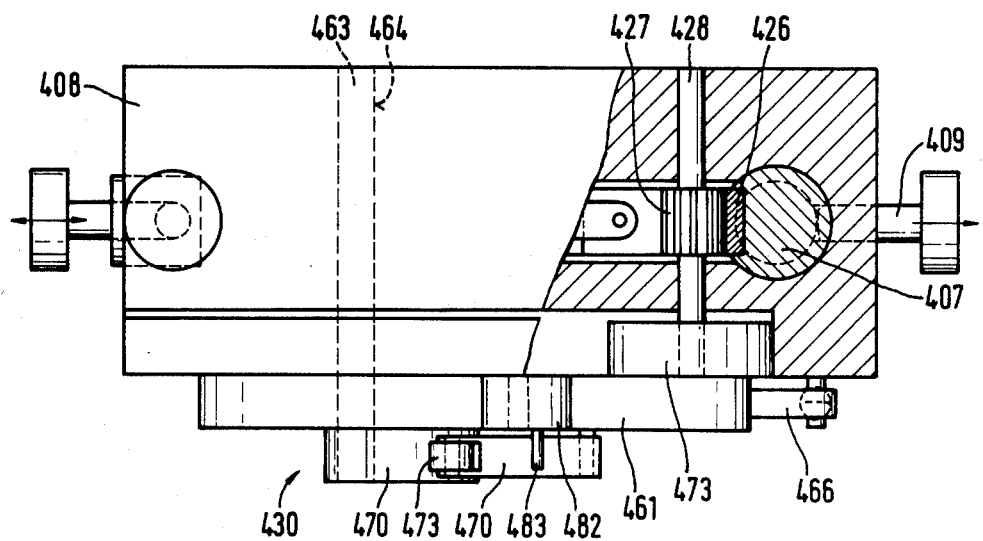

The fourth embodiment of the device according to the invention according to FIGS. 16 and 17, uses a power storage device to move injection rod 407, which corresponds to the toothed-belt/tension spring power storage device 326, 350 of the embodiments shown in FIGS. 14 and 15. In this fourth embodiment under discussion, the locking device also corresponds to the embodiment shown in FIGS. 14 and 15 as well as those shown in FIGS. 12 and 13. For this reason there is no need to discuss separately the design and operation of these components of the injector device.

In the fourth embodiment shown here, a power storage device 430 is provided which operates using the same pinion 427 on injection rod 407 by means of which the above-mentioned power storage device in the form of toothed belt 426 and the tension spring acting on the latter (not shown) drives injection rod 407. Power storage device 430 has a toothed belt 460 which is non-rotatably mounted on the end of rotational shaft 428, which is brought out of free-running element 437. A continuous toothed belt 461 runs over belt gear 460, said belt meshing with a second gear 462 with approximately four times the diameter of gear 460. Gear 462 is rotatably mounted by means of a shaft 463 in a bearing bore 464 in injector holder 408. A tensioning roller lever 466 with a tensioning roller 467 rotatably mounted thereon is pivotably mounted on a bearing pin 465, located on the front surface of injector holder 408, and is under the influence of a pretensioned tension spring 468, so that tensioning roller 467 forced against toothed belt 461 creates a specific, constant pretension in it.

A cam 470 in the form of a 180° sector of a circle is mounted on the end of axis 463 which projects out of the end of the second belt gear 462 or on the end of gear 462, non-rotatably mounted and rotatable as a unit with gear 462, said cam forming a curved surface both with its circular circumferential surface 470a and a radial surface 470b. The two surfaces 470a and 470b are connected together at the corner of the sector of the circle by a rounded surface 470c. A pivot lever 472 is pivotably mounted in a vertical plane on a bearing pin 471 which rests on the front surface of injector holder 408, said lever abutting the curved surface 470a of cam 470 by a tensioning roller 473 which is rotatably mounted at its end. Lever 472 is tensioned by a pretensioned tension spring 474 which constitutes a second power storage device.

A circular eccentric cam 481 is rotatably mounted in a manner not shown in greater detail on injector holder 408 above the upper run of toothed belt 461 by means of a shaft 480. Eccentric cam 481 has a roller 482 on its outer circumference, in other words a ball bearing. A handle 483 projects forward from the forward surface of eccentric cam 481 by means of which eccentric cam 481 together with its shaft 480 can be rotated. Shaft 480 is held with sufficient friction in the hole, not shown, of injector holder 408 that eccentric cam 481 is in a position to retain its rotational position, once set, even against a return force generated by toothed belt 461. The spacing of shaft 480 from the upper run of toothed belt 461 is selected so that roller 482 always rests on the upper run of the toothed belt, whereby a rotation of eccentric cam 481 produces a more or less pronounced deflection of the toothed belt downward.

The operation of this fourth embodiment is as follows: in the initial position of injection rod 407 shown in FIG. 16, tensioning roller 473 of pivot lever 472 abuts surface 470a located concentrically with respect to shaft 463. The point of contact of tensioning roller 473 with curved surface 470a thus assumes a distance which is fixed, measured in the circumferential direction, from the transition of the rounded curved surface segment 470c to the rectilinear curved surface segment 470d, which corresponds to the length of the travel of specimen 406 until it makes its first contact with the metal mirror, not shown. Since the length of this travel path, in view of the anticipated different heights of different specimens 406, is not always the same, eccentric cam 481 provides the opportunity for compensating for resultant variations in the vertical distance a of the underside of specimen from the specimen holder 405 and for the corresponding fluctuations in the length of the travel path. For this purpose, eccentric cam 481 is rotated initially until toothed belt 461 is moved and deflected downward to a sufficient degree by roller 482 pressing upon it. This deflection results is a corresponding rotation of second gear 462 and cam 470 firmly attached thereto in a clockwise direction so that accordingly the distance between the contact point and the rectilinear curved surface segment 470b is adjusted, in other words is shortened by the above-mentioned downward deflection of belt 461.

When injection rod 407 is released in the manner already described above by pulling trigger pin 409, so that the first power storage device consisting of toothed belt 426 and the tension spring, not shown but acting thereon, can become effective, injection rod 407 moves downward with acceleration. During the downward movement, toothed belt 426 meshes with gear 427 (as already described in connection with FIGS. 14 and 15 with reference to the embodiments shown in FIGS. 12 and 13), so that as a result the linear movement of injection rod 407 is converted into a rotation of rotational shaft 428 and hence of gear 460. By means of belt 461 this drives second gear 462 and hence cam 470, so that cam 470 rotates clockwise beneath contact roller 473. As a result of the adjustment of roller 473, as described above, the latter reaches the rounded curved surface segment 470c essentially at the same time as specimen 406 touches the metal mirror. While, prior to this point, the spring constituting the second power storage device 474 has not been able to exert any torque on cam 470 via pivot lever 472, so that apart from the effect of friction the velocity of injection rod 407 has not been influenced by it, when pressure roller 473 rolls on the rounded curved surface segment 470c on cam 470 and hence on gear 462, an increasing circumferential force is applied by tensioning roller 473. This circumferential force is transmitted by belt 461, gear 460, shaft 428, and gear 427 to injection rod 407, and immediately after contact of specimen 406 with the metal mirror, creates the necessary application pressure described at the outset, which prevents bending of the suddenly frozen contact surface of specimen 406. The modified position of pivot lever 472 and tension roller 473 as well as cam 470 is shown by the dashed lines in FIG. 16.

It will be understood that when specimen 406 strikes the metal mirror, free-running element 437 has also become effective in the sense that it prevents rebound, as already described in connection with FIGS. 12 and 13. The release of free-running element 437 in the manner described above allows injection rod 407, after complete freezing of specimen 406, to be returned to the initial position shown in FIG. 16, for example until specimen holder 405 strikes the underside of injector holder 408.

In the fifth embodiment of the device according to the invention shown in FIG. 18, once again only those parts of the injector device and of the metal mirror are shown which are important for an understanding of the operation of the invention. In this embodiment, in an injector holder 508 made in the form of a cylinder, an injection rod 507 in the form of a hollow piston is received, slidably, displaceably and in a sealed fashion, so that it can be energized from above by a line 550 containing pressure medium 551, which can be pneumatic or hydraulic. In its upper end segment, injection rod 507 is provided on its outside with a sawtooth profile 526 whose teeth are directed diagonally upward. A hollow, cylindrical slide guide for a locking element 518 is mounted laterally on injector holder 508, said locking element bearing at the end facing injection rod 507 a brush unit 526' whose bristles are aligned opposite to the saw teeth of sawtooth profile 526. Locking element 518 is tensioned by a compression spring 520 so that brush unit 526' abuts the outer surface of injection rod 507 with a certain degree of pretensioning. A handle 521 is connected by a shaft with locking element 518, by means of which locking element 518 can be pulled away from injection rod 507 against the force of spring 520 (see arrow). Locking element 518 combined with the parts attached to it and sawtooth profile 526 produces a locking device which is represented as a whole by 513.

To control the amount of pressure applied to injection rod 507 by pressure medium 551, a pump 552, control valve 553, and control device 554 are provided. Control device 554 includes a light beam 555 associated with metal mirror 502, composed of a light source 556 and a receiver 557. Light source 556 and receiver 557, as indicated by the double arrows, are adjustable heightwise relative to metal mirror 502. By a line 558, receiver 557 transmits output signals to control device 554, when light beam 555 is broken by specimen 506. An adjustment scale with a selector element 559 is provided on control device 554, by means of which the pressure of pressure medium 551 can be selected by appropriately controlling pump 552. Control device 554 is connected by lines 560 with control valve 553 and by a line 561 with pump 552.

In the state shown in FIG. 18, injection rod 507 is held in injector holder 508 by a lateral force exerted by locking element 518 and by a certain resultant pretensioning in its initial position. As a result of a command from control device 554, which can be triggered, for example, by pressing a button 562, control valve 553 is controlled and opened thereby. As a result, injection rod 507 is exposed through line 550 from pump 552 with pressure medium at a predetermined first pressure, said pressure being adjusted on selector element 559. Depending on the amount of pressure medium supplied by pump 552, injection rod 507 extends until specimen 506 breaks light beam 555 a short distance before striking metal mirror 502. Thereupon, receiver 557 transmits a corresponding signal to control device 554 whereupon the latter, in turn, controls pump 552 in order to increase its initial pressure to a certain second pressure value. The resultant time delay until the pressure rises from the first to the second pressure value can be taken into account by adjusting light beam 555 relative to metal mirror 502 in such fashion that after the initial contact of specimen 506 with metal mirror 502 the increased pressure is immediately applied to injection rod 507 and therefore ensures a continuuous surface contact until specimen 506 is completely frozen. Rebounding of injection rod 507 is prevented by locking device 513 with brush unit 526' engaging sawtooth profile 526, as described above. After specimen 506 is completely frozen, control valve 553 can be brought to a drain position, not shown, in which line 550 has zero pressure and the line segment 550a leading to pump 552 is once again blocked. At this point, injection rod 507 can be pushed back into its initial position.

The circuit of control device 554 for achieving the function described above is not shown in detail, since it is evident to the individual skilled in the art from its manner of operation. In addition, it is also understood that, despite the merely schematic representation of metal mirror 502, the latter is designed and disposed in the same fashion as is the case in conjunction with the metal-mirror cryofixation devices according to the state of the art described at the outset.

The sixth embodiment according to FIG. 19 differs from the fifth embodiment according to FIG. 18 in the type of drive for injection rod 607. Locking device 613, however, is designed in the same fashion and operates in the same way as the one in the embodiment shown in FIG. 18, so that a detailed explanation is not necesary here.

Injection rod 607 slidably guided in injector holder 608 is connected at its upper end with a permanent magnetic rod 607', surrounded by a magnetic coil 650. Magnetic coil 650 is connected by leads 651, 652 with a control device 654, which contains a power supply or a connection to the power line. The length of permanent magnetic rod 607' exceeds the length of travel of specimen 606 until it reaches metal mirror 602, so that even when injection rod 607 is fully lowered, permanent magnetic rod 607' still extends for a considerable distance into magnetic coil 650, in order to be actuatable under control. A contact sensor 655 adjustable heightwise is provided in the vicinity of metal mirror 602, said sensor being mountable, for example, on the holder which is not shown but which surrounds metal mirror 602 and which lies along the path of movement of a contact strip 656 fastened to injection rod 607 above specimen 606. Contact sensor 655 is connected by a lead 657 with control device 654 in order to trigger an output signal to the latter upon contact with contact strip 656.

Injection rod 607 can be held in the starting position shown in FIG. 19 once again by pretensioning by means of locking device 613 and the corresponding hole of injector holder 8. In the present embodiment, however, the initial position of injection rod 607 is retained by a corresponding tensioning of magnetic coil 650, whereby the magnetic field produced by magnetic coil 650 pulls permanent magnetic rod 607' upward so that specimen holder 605 abuts the underside of injector holder 608. Pressing a button 658 on control device 654 now triggers injection, whereupon the direction of flow of current through magnetic coil 650 is reversed and the injector is expelled downward under the influence of the magnetic force. In this connection, the strength of the current in magnetic coil 650, which can be selected on control device 654 in advance, determines the velocity of injection rod 607 and enhances that of specimen 606 when its strikes metal mirror 602. In advance, contact sensor 655 can be so adjusted as a function of the height of specimen 606 that contact strip 656 strikes contact sensor 655 as soon as or shortly before specimen 606 comes in contact with metal mirror 602. When contact sensor 655 is contacted by contact strip 656, the former delivers an output signal to control device 654, which causes the control device to increase the current floating through magnetic coil 650. The increased current subsequently leads to an increase in the force exerted on injection rod 607 by magnetic coil 650, and this in turn, even after injection rod 607 is braked, produces the necessary application pressure which prevents deformation of specimen 606 at its marginal zone after freezing. When specimen 606 is frozen all the way through, after actuating a button 659, magnetic coil 650 can be polarity-reversed so that injection rod 607 can be retracted upward into its starting position once more.

The signal from contact sensor 655 can be processed in control device 654 with a fixed and possibly preselectable delay, in order thereby to be able to control the point in time at which the pressure is increased by the intensified magnetic field in a certain fashion.

Here again the circuit design of control device 654 and its cooperation with contact sensor 655 will be apparent to the individual skilled in the art of control from the function described, so that we can eliminate a description of the circuit.

The above-described embodiments of the device according to the invention by means of which the method according to the invention can be worked eliminate the initially described disadvantages of the state of the art in a relatively simple manner. This means that in the first place, undesirable rebound of the specimen off the metal mirror is prevented by the use of rebound locks which prevent reversal of the direction of movement of the injection rod even when, as is specifically intended by the invention, the velocity used and the mass of the injection rod or the spring force acting on the injection rod are kept as low as possible to protect the specimen. In addition, and independently of these return locks or locking devices, by mechanical, pneumatic, hydraulic, or magnetic means, following the critical initial contact between the specimen and the metal mirror, a sufficient application pressure is produced. Since the critical marginal zone has vitrified already in the millisecond range after this initial contact, a force of practically any magnitude can be built up secondarily in order to maintain a permanent solid contact between the perfectly vitrified marginal zone of the specimen and the metal mirror until the specimen has reached a sufficiently low temperature throughout its spatial extent with the adjoining parts of the specimen holder. This temperature is sufficient when a harmful conversion from the amorphous-vitrified state to the crystalline state (devitrification temperature approximately $-135°$ C.) or a harmful recrystallization of the microcrystalline-hardened, aqueous, mixed phases of the specimen, whose recrystallization range is above $-80°$ C., is reliably prevented.

Although this is not shown in the embodiments, one advantageous additional embodiment of all the devices associated with a locking device can consist in the fact that they are equipped with a pneumatic damping device as shown in FIG. 6 (see also German Patent Application No. P 3532446.5). It is in injection systems with a lower carrier mass of the injection rod as well as smaller force of the power storage device accelerating the injector, for example the spring, that the otherwise advantageous pneumatic damping produces a pronounced rebound as a result of the air enclosed in the injection rod which is made in the form of a cylinder. Since, however, the locking devices described suppress rebound, the combination of the pneumatic damping described with one of the locking devices described as well as one of the power storage devices described for producing pressure, produces an optimally adjustable system. In particular, it is possible when using sufficiently thick and sufficiently elastic intermediate layers between the specimen and the specimen holder on the injection rod designed in the form of a hollow cylinder to do away with spacer rings on the metal mirror, which normally considerably complicate work and make the quality of the results dependant on the height adjustment described in conjunction with FIG. 3.

Within the scope of the invention, changes can be made to the embodiments described above. Thus it is fundamentally possible to provide locking devices and power storage devices of the type described on a movable metal mirror, which is moved with respect to a fixed specimen. In addition, the course of the injection process, especially the controlled injection process in the embodiments shown in FIGS. 18 and 19, can be largely automated. It is also possible, for example in the embodiments shown in FIGS. 16 and 17, to adjust the power storage device to the length of the travel path of the specimen using positioning elements whose scale is calibrated directly in length values of the travel path of the injection rod. This is applicable, for example, to the adjustment of eccentric cam 481 in the embodiment shown in FIGS. 16 and 17.

It is also possible to pre-select the critical parameters for cryofixation, especially the velocity with which the specimen strikes the metal mirror or vice versa, as well as the application pressure between the specimen and the metal mirror during cryofixation, pre-selecting it in an electrical fashion and executing it by electrical components, for example, electric motors. During the process, the pre-selected and/or achieved values can be displayed either in analog or digital fashion. It is also possible to adjust the various power storage devices by control elements, for example, positioning motors.

Finally, the devices can also be simplified in design. Thus, for example, instead of cam 470 and spring-loaded pivot lever 472 in the fourth embodiment as shown in FIGS. 16 and 17, a spring can act eccentrically and directly on gear 462. It is also possible to have a direct gear coupling without toothed belts located therebetween.

Finally, for the above-described combination of a locking device (rebound lock) with a pneumatically damped specimen holder according to FIG. 6, special protection is also claimed for the case in which a power storage device is not provided for generating application pressure.

We claim:

1. Method for metal-mirror cryofixation of bio-medical or similar technical specimens wherein a specimen mounted on a specimen holder is moved at a specified speed relative to a cooled, highly polished, solid surface (metal mirror) until contact takes place between the specimen and metal mirror, whereby the movement is braked until it is zero, and the specimen and the metal mirror are pressed against one another with a force corresponding to the braking, and wherein the specimen and metal mirror are kept in mutual contact, whereby at least the marginal zone of the specimen in contact with the metal mirror is suddenly cooled to the temperature of the metal mirror, characterized by the fact, that the specimen and the metal mirror, immediately after initial contact, are pressed against one another by an additional force independent of the velocity or the braking, until the specimen is completely frozen.

2. Method according to claim 1, characterized by the fact that the additional force is so dimensioned that a pressure of at least 0.5 kg/cm² prevails at the contact surfaced between the specimen and the metal mirror.

3. Method according to claim 1, characterized by the fact that the speed at which the specimen is moved relative to the metal mirror is so dimensioned that the additional force exceeds the force created by the braking of the movement.

4. Device especially according to claim 1, characterized by the combination of a locking device to prevent rebound of the specimen holder following impact of the specimen against the metal mirror with a pneumatic damping device supporting the specimen holder to reduce the force acting on the specimen on impact.

5. Device according to claim 1, characterized by the fact that the specimen holder and the associated part of the damping device has a mass of 20 g maximum.

6. Device according to claim 1, characterized by the fact that a locking device (113; 126', 126''; 144, 145; 237; 513; 613) is provided to prevent rebounding of the specimen holder following impact between the specimen and the metal mirror.

7. Device according to claim 6, characterized by the fact that the locking device has teeth (126) provided on injection rod (107, 107') which holds the specimen holder or brushes (126') with diagonal bristles as well as a locking latch (118, 118') cooperating therewith.

8. Device according to claim 6, characterized by the fact that a running surface (140) is provided on injection rod (107''), said surface delimiting a wedge-shaped slot (143) in conjunction with a fixed matching surface (142) into which a clamping roller (144) is urged by spring tension (145) in such fashion that the specimen holder is prevented from moving backward.

9. Device according to claim 6, characterized by the fact that the locking device is free-running clutch (237) which is coupled to specimen holder (205, 207) through a drive stage (226, 227).

10. Device for metal-mirror cryofixation for working the method according to claim 1 with a cooled, highly polished solid surface (metal mirror), with a specimen holder, with a positioning device for movable positioning of the specimen holder or the metal mirror and for its guidance along a movement path connecting the specimen holder and the metal mirror under the influence of gravity and/or a power-generating device, and with a locking device to prevent separation of the specimen in the metal mirror caused by rebound following their mutual contact at the end of the travel path, characterized by the fact that a power-generating device (130; 430; 507, 550, 552; 607', 650) is provided to press the specimen and metal mirror together, said device being controllably actuatable after contact between the specimen and metal mirror.

11. Device according to claim 10 wherein the power-generating device for driving the specimen holder and/or metal mirror is a power storage device, characterized by the fact that an additional power storage device (130, 430), independent of the first power storage device (110, 210, 350), is provided to press the specimen and metal mirror against one another.

12. Device according to claim 10, characterized by the fact that the power-generating device (550, 552; 650) for driving an injection rod (507, 607) supporting the specimen holder is controllable by a control (554, 555; 654, 655) from a first force value to a second force value.

13. Device according to claim 10, characterized by the fact that a curve (136, 470) is provided on which a curve-following element (134, 473) is pressed by the additional power-generating device (135, 474) during the relative movement of the specimen and metal mirror, and by the fact that the curve (136, 470) has a shape such that it is only during or after the contact between the specimen and the metal mirror that the additional power-generating device exerts, by means of the curve-following element, a force in the direction of the above-mentioned movement path upon specimen holder (105, 405).

14. Device according to claim 13, characterized by the fact that the curve-following element (134) has a roller located at one end of a spring-loaded swivel lever (133), and by the fact that the curve (136) is formed on an axially displaceable shaft part (125) of the specimen holder and runs in a first segment (136) parallel to the shaft axis, and in a second segment (136a) in an arc into the shaft end (136b) which is perpendicular to the shaft axis.

15. Device according to claim 13, characterized by the fact that the cam (136, 470) is adjustable to fit the length of the travel path.

16. Device according to claim 13, characterized by the fact that the curve (470a, b, c) is designed with a cam (470) which is rotatable in synchronization with the movement of specimen holder (405, 407) and is drivably connected by a drive stage (460, 426) with specimen holder (405, 407).

17. Device according to claim 16, characterized by the fact that the drive stage comprises a rack or a stretched, toothed belt (426), which is disposed axially parallel with an injection rod (407) bearing specimen holder (405), as well as a pinion gear (460, 427) tensionable by the additional power storage device.

18. Device according to claim 16, characterized by the fact that the first power storage device as well (350), for driving specimen holder (405, 407), is drivably connected by drive stage (426, 427) with specimen holder (405, 407).

* * * * *